United States Patent [19]  
Eberl et al.

[11] Patent Number: 4,681,587
[45] Date of Patent: Jul. 21, 1987

[54] MASTOPROSTHESIS

[75] Inventors: Tertulin Eberl, Penzberg, Fed. Rep. of Germany; Georg Weber-Unger, Kufstein, Austria

[73] Assignee: Anita-Spezialmiederfabrik Dr. Helbig & Co., Kufstein, Austria

[21] Appl. No.: 794,702

[22] Filed: Nov. 4, 1985

Related U.S. Application Data

[63] Continuation of Ser. No. 600,483, Apr. 16, 1984, abandoned.

[30] Foreign Application Priority Data

Apr. 18, 1983 [DE] Fed. Rep. of Germany ... 8311438[U]

[51] Int. Cl.4 .............................................. A61F 2/12
[52] U.S. Cl. ...................................................... 623/7
[58] Field of Search ......................................... 623/7, 8

[56] References Cited

U.S. PATENT DOCUMENTS 3,568,681  3/1971  Comollo ................................. 623/7
3,641,592  2/1972  Den Bleyker ......................... 623/7
3,706,104  12/1972  Dehlin et al. ........................ 623/7
3,811,133  5/1974  Harris .................................... 623/7
4,172,298  10/1979  Rechenberg .......................... 623/7

FOREIGN PATENT DOCUMENTS 2742394  3/1979  Fed. Rep. of Germany .......... 623/7
2451738  11/1980  France ................................. 623/7

Primary Examiner—Richard J. Apley
Assistant Examiner—David Isabella
Attorney, Agent, or Firm—Zarley, McKee, Thomte, Voorhees & Sease

[57] ABSTRACT

A mastoprosthesis consists of a soft synthetic material member (1) formed after the shape of a natural breast, which member is provided on its back side with a cavity (2), into which a pad member (3) is inserted, which may consist of foam material or of fibers. The pad member (3) is held within cavity (2) for example by means of a rebound (or back salient) means (5) on the synthetic material member (1).

10 Claims, 4 Drawing Figures

U.S. Patent      Jul. 21, 1987      4,681,587
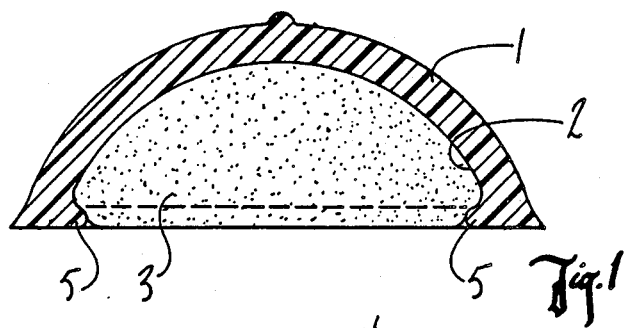
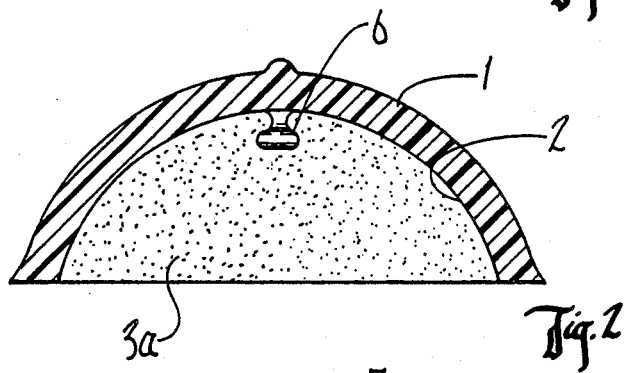
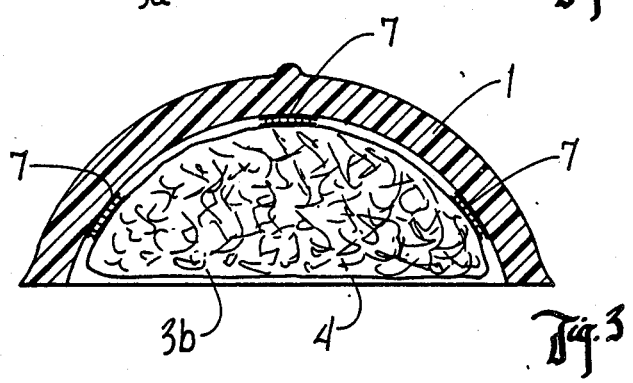
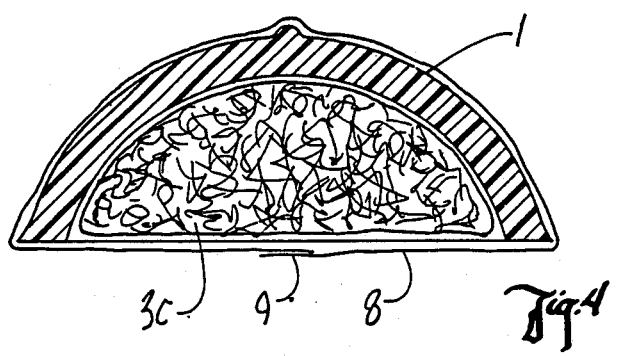

MASTOPROSTHESIS

This is a continuation of application Ser. No. 600,483, filed Apr. 16, 1984, now abandoned.

The invention relates to a mastoprosthesis made of a soft synthetic member formed to have the shape of a natural breast, which synthetic member on its back side includes a cavity.

Following mastectomy due to carcinosis, the patient is in need of a breast prosthesis, the outer surfaces of which are formed to have the shape of a breast, and which consists of a synthetic material composition, which as to its consistency and its speific weight approximately corresponds to the natural breast. The back side of the mastoprosthesis as a rule is provided with a concavity for the purpose of reducing the weight of the prosthesis, since, frequently, solid prostheses made of conventional synthetic materials are found by the wearers to be too heavy.

The drawback which the concavities involve, however, is that the mastoprosthesis gets the tendency to collapse, when worn in a bra, in a manner such that the upper part slips down. This difficulty can be overcome in that a less soft plastic material is used, which of course involves the drawback that it is in that way deviated from the softness of a natural breast. The suggestion has also been made to form the plastic member on the back side of the prosthesis, in particular the part surrounding the cavity, of a material made to be harder. That measure, however, makes production of the prosthesis more difficult.

A drawback which all prostheses consisting of a synthetic material member have in common is that the synthetic materials that come into consideration therefor, especially silicon rubber, are disproportionately expensive, so that the price to be paid for these prostheses also is comparatively high.

The invention was based on the object to improve a mastoprosthesis of a soft synthetic material member formed to have the shape of a natural breast, which includes a cavity on its back side, in a manner such that the tendency to collapse is reduced. Moreover, it was intended to attain a reduction in costs.

This object is accomplished according to the invention in that in the case of the mentioned prosthesis a pad member is inserted into the cavity. The pad member prevents collapsing of the prosthesis. Moreover, it allows making the cavity substantially larger, so that considerably less synthetic material is used to produce the prosthesis, without said prosthesis in that respect losing its stability and its consistency.

The synthetic material body may be covered in per se known manner with a film, as the synthetic materials that are of suitable softness customarily tend to stick. It is preferred to use in per se known manner silicon rubber for the synthetic material member and polyurethane for the film.

The padding member may consist of foam material, such as, for example, of a foamed polyurethane shaped member. It is also possible, however, for the padding member to consist of fibers, for example, of a cotton swab. Said swab of cotton may, for example, be enclosed within a fabric bag.

The pad member may be securely connected to the synthetic material member. However, the two members preferably are releasably joined together. That is desirable because the pad member tends, due to its porous structure, to become soiled. Hence, it needs to be washed from time to time or to be entirely replaced.

The connection between the synthetic material member and the pad member may take place in form-locked manner, for example, in that the cavity includes a rebound means above the plane of the back side of the synthetic material member or has other undercuts, into which the pad member extends. It is, however, also possible to position one or more mushroom-type projections on the surface of the cavity of the synthetic material member, which snap into corresponding recesses in the pad member.

Besides connection by form-locking, other means of connection, such as for example Velcro strip fasteners, also come into consideration.

According to another advantageous further development, the synthetic material member and the pad member are both positioned within a fabric pouch. The fabric pouch may, for example, have a slot-like opening on its back side, out of which the pad member and optionally also the synthetic material member may readily be taken.

The attached FIGS. 1 to 4 show sections taken through preferred embodiments of the mastoprosthesis of the invention.

The embodiment of FIG. 1 has a synthetic material member 1 with a cavity 2, into which is inserted a shaped member 3 made of a foamed plastic material. Retention of said shaped member 3 is brought about in that it extends into the rebound means 5 that encircles the cavity 2.

In the embodiment of FIG. 2, a mushroom-type projection 6 is located within the cavity 2 on the synthetic member 1, which projection extends into a corresponding recess of the foam material member 3a.

The embodiment of FIG. 3 also includes a synthetic material member 1. The pad member 3b consists of a cotton swab that is positioned within a fabric bag 4. The two members are joined with the aid of a Velcro strip fastener 7.

In the embodiment according to FIG. 4, the synthetic material member 1 is enclosed, together with the pad member consisting of a cotton swab 3c, within a fabric pouch 8, which is provided on its back side with a slot-like opening 9, in the region of which two fabric layers are overlapping.

I claim:

1. A mastoprosthesis for wearing within a brassiere by a person having mastectomy scar tissue located rearwardly of said brassiere, said mastoprosthesis comprising:

a body comprising an inner solid core of a soft silicone material resembling in its consistency and specific weight the natural breast tissue, and an outer film covering said core completely, said body having a front surface which is contoured to conform to the shape of a female breast and a rear surface defining a depression which is contoured to conform substantially to the contour of said front surface, a single one piece backing member of a soft resilient material inserted in said depression, said backing member being lighter in specific weight than said body and having a front surface and a rear surface, said front surface of said backing member facing and conforming substantially to the rear surface of said body, retaining means for releasably retaining said backing member within said depression of said body, said depression having a rearwardly facing opening sufficiently large to permit insertion and removal of said backing member into said depression;

said retaining means comprising a fabric enclosure member which covers the front surface of said body and said rear surface of said backing member so as to retain said backing member within said depression, said fabric enclosure member including two overlying flap portions which are adapted to be separated from one another so as to define an opening through which said body and said backing member can be removed from the enclosure member and inserted again into it;

said rearwardly facing opening being substantially free of said silicone material of said body so as to minimize interference of said silicone material of said body with said scar tissue and so as to expose substantially said entire rear surface of said backing member rearwardly toward said scar tissue of said person through said rearwardly facing opening of said depression.

2. The mastoprosthesis of claim 1 wherein said backing member comprises foam material.

3. The mastoprosthesis of claim 1 wherein said backing member comprises fibers.

4. The mastoprosthesis of claim 1 wherein said backing member is enclosed within a bag within said depression.

5. The mastoprosthesis of claim 4 wherein said male portion comprises at least one mushroom-like projection on said rear surface of said cavity of said body.

6. A mastoprosthesis for wearing within a brassiere by a person having mastectomy scar tissue located rearwardly of said brassiere, said mastoprosthesis comprising, a body consisting of an inner solid core of a soft synthetic material resembling in its consistency and specific weight the natural breast tissue and an outer film covering said core completely, said body having a front surface which is contoured to conform to the shape of a female breast and a rear surface defining a cavity which is contoured to conform substantially to the contour of said front surface, said cavity having a rearwardly presented opening;

a single one piece pad member inserted into said cavity, said pad member being lighter in specific weight than said body, and having a front surface and a rear surface, said front surface of said pad member facing and substantially conforming to said rear surface of said body;

said rearwardly presented opening of said cavity being sufficiently large to permit said pad member to be inserted into and removed from said cavity;

said solid core being formed of silicon and said outer film being of polyurethane, said body and pad member being releasably attached to one another;

said rearwardly presented opening of said cavity being substantially free of said silicone of said body so as to minimize interference of said silicone of said body with said scar tissue and so as to expose substantially said entire rear surface of said pad member rearwardly toward said scar tissue of said person through said rearwardly facing opening of said cavity.

7. The mastoprosthesis of claim 6 wherein said body and said pad member are formed as interlocking male and female portions for releasable attachment to one another.

8. The mastoprosthesis of claim 6 wherein said body includes a lip positioned around said rearwardly presented opening of said cavity for engaging said pad member and retaining said pad member within said cavity.

9. The mastoprosthesis of claim 6 wherein said body and said pad member are connected together through a Velcro strip fastener.

10. The mastoprosthesis of claim 6 wherein said body and said pad member are connected together by a fabric pouch which surrounds both of said body and said pad member.

* * * * *